United States Patent [19]

Papenfuhs et al.

[11] Patent Number: 4,960,940
[45] Date of Patent: Oct. 2, 1990

[54] BIS(HYDROXYETHYLSULFONYLMETHYL)ANILINES AND A PROCESS FOR THEIR PREPARATION

[75] Inventors: Theodor Papenfuhs, Frankfurt am Main; Josef Geisenberger, Kelkheim, both of Fed. Rep. of Germany

[73] Assignee: Hoechst Aktiengesellschaft, Frankfurt am Main, Fed. Rep. of Germany

[21] Appl. No.: 251,469

[22] Filed: Sep. 29, 1988

[30] Foreign Application Priority Data

Oct. 3, 1987 [DE] Fed. Rep. of Germany ....... 3733504

[51] Int. Cl.$^5$ ............................................. C07C 317/26
[52] U.S. Cl. ..................................... 564/440; 568/30; 568/32; 568/46
[58] Field of Search ............................. 568/30, 32, 46; 504/440

[56] References Cited

U.S. PATENT DOCUMENTS

| | | |
|---|---|---|
| 3,201,434 | 8/1965 | Tesoro ................................... 568/32 |
| 3,394,154 | 7/1968 | Braus et al. ........................... 568/46 |
| 3,449,439 | 6/1969 | Kuhnen et al. ....................... 568/32 |
| 4,612,394 | 9/1986 | Katero et al. ....................... 564/440 |

FOREIGN PATENT DOCUMENTS

| | | |
|---|---|---|
| 3314565 | 10/1984 | Fed. Rep. of Germany ....... 564/440 |
| 931595 | 7/1963 | United Kingdom ................ 564/440 |

*Primary Examiner*—James H. Reamer

[57] ABSTRACT

A process for the preparation of compounds of the formula

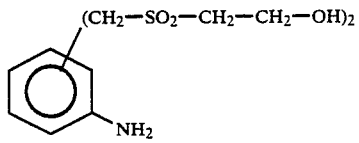

in which the side chains —$CH_2$—$SO_2$—$CH_2$—$CH_2$—OH are in the ortho-, meta- or para-position relative to one another and the amino group is in the 4-position in the case where the two side chains are in the 1,2- or 1,3-position, by reacting 1 mol of xylylene dichloride with at least 2 mol of mercaptoethanol at 40°–150° C. in an aqueous medium in the presence of an acid-binding agent to give the corresponding compound of the formula

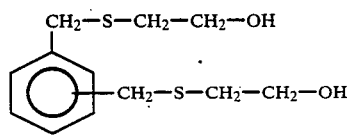

oxidizing this product with at least 4 mol of hydrogen peroxide at 50°–120° C. at a pH<7 in the presence of tungsten(VI) compounds to a compound of the formula

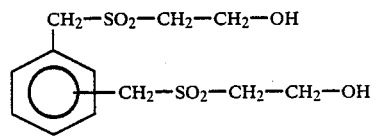

converting this product with anhydrous sulfuric acid at 30°–45° C. to the corresponding bis(sulfuric ester), nitrating the latter with high-percentage nitric acid at 0°–60° C. to give the bis(sulfatoethylsulfonylmethyl)nitrobenzene, hydrolyzing this product after the addition of water by heating followed by reduction.

9 Claims, No Drawings

BIS(HYDROXYETHYLSULFONYLMETHYL)ANILINES AND A PROCESS FOR THEIR PREPARATION

The present invention relates to novel bis(hydroxyethylsulfonylmethyl)anilines and a process for their preparation. The novel compounds are useful precursors for the preparation of fiber-reactive dyes.

The novel compounds of the general formula (I) mentioned below and precursors thereof of the general formula (II) (see below) have not yet been described in the literature. GB Patent No. 931,595 merely discloses a derivative of (I) (4-amino-2,6-bis(hydroxyethylsulfonylmethyl)toluene, which is said to be a precursor for fiber-reactive dyes. Its preparation is carried out in an ecologically unfavorable manner by chloromethylation of 4-nitrotoluene to give 4-nitro-2,6-bis(chloromethyl)toluene, which is then reacted in a manner known per se by chlorine exchange with mercaptoethanol, oxidation with hydrogen peroxide and reduction with iron to give the final product.

This synthetic sequence uses, as the key step, the industrially unsatisfactory chloromethylation of nitroaromatics by means of formaldehyde/hydrochloric acid (with the formation of dichlorodimethyl ether whose disposal absolutely requires large technical expenditures), allows only the introduction of reactive substituents in the m-position with respect to the nitro group (and amino group) and requires solvents in the chlorine exchange step (cf. Example 4 of the abovementioned GB patent).

In contrast, the compounds according to the invention of the general formula (I) in which R and X denote hydrogen atoms and which are structurally different from the known compound in that at least one reactive group is not in the m-position relative to the nitro (or amino) substituent can be prepared from bis(chloromethyl)benzenes, which are readily available industrially by side chain chlorination of the isomeric xylenes, followed by purification through distillation.

The characteristic feature of the synthetic sequence of the present invention is the fact that the nitrogen function is introduced into the molecule only after the reactive groups have been synthesized, which results in a substitution pattern which is different from that of the state of the art. In addition, the change in the order of the process steps makes it possible to carry out all steps in the absence of solvents. The novel compounds and processes for the preparation thereof therefore allow a wider range of substituents relative to one another and make possible an industrial synthesis without the use of solvents and by means of conventional apparatuses from precursors which can be synthesized without any ecological difficulties.

Accordingly, the present invention relates to novel bis(hydroxyethylsulfonylmethyl)anilines of the general formula (I)

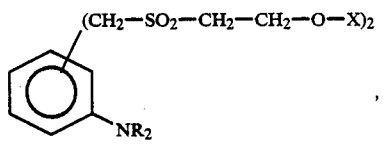

in which R and X denote hydrogen atoms, the two side chains —CH₂—SO₂—CH₂—CH₂—O—X are in the ortho-, meta- or para-position relative to one another and the —NR₂ group is in the 4-position in the case where the two other substituents are in the 1,2- or 1,3-position, and to a process for their preparation by reacting 1 mol of xylylene dichloride (1,2-, 1,3- or 1,4-bis(chloromethyl)benzene) with at least two mol of mercaptoethanol at temperatures from about 40° to about 150° C., preferably about 70° to about 120° C., in an aqueous medium (in the absence of organic solvents) in the presence of an acid-binding agent to give the corresponding bis(hydroxyethylmercaptomethyl)benzene of the general formula (II)

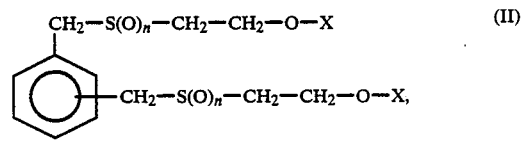

in which X denotes a hydrogen atom and n denotes the number 0, and the two side chains are in the ortho-, meta- or para-position relative to one another, oxidizing this intermediate after or preferably without isolation with at least 4 mol, preferably 4.4 to 5.6 mol, of hydrogen peroxide at temperatures from about 50° to about 120° C., preferably about 80° to about 100° C., at a pH of <7, preferably <4, in the presence of tungsten (VI) compounds as a catalyst to give the corresponding bis(hydroxyethylsulfonylmethyl)benzene of the abovementioned general formula (II), in which X denotes a hydrogen atom and n denotes the number 2, converting this product with at least 4 mol, preferably 5 to 7 mol, of anhydrous sulfuric acid at temperatures from about 30° to about 45° C. to the corresponding bis(sulfuric ester) of the general formula (II) mentioned, in which X denotes the group —SO₃H and n denotes the number 2, nitrating the latter with at least the stoichiometric amount of high-percentage nitric acid, possibly as a mixture with anhydrous sulfuric acid, at temperatures from about 0° to about 60° C., preferably about 25° to about 45° C., to give the bis(sulfatoethylsulfonylmethyl)nitrobenzene of the formula (III)

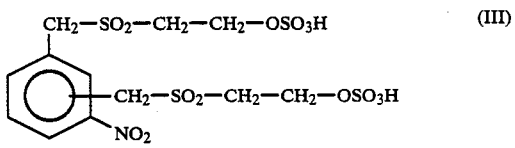

in which the two side chains —CH₂—SO₂—CH₂—CH₂—OSO₃H are in the ortho-, meta- or para-position relative to one another and the nitro group is in the 4-position in the case where the two side chains mentioned are in the 1,2- or 1,3-position, hydrolyzing this product after the addition of water by heating, advantageously at temperatures from about 100° to about 120° C., to give the corresponding bis(hydroxyethylsulfonylmethyl)nitrobenzene and reducing the latter, after isolation of the intermediate, with iron in an aqueous medium or preferably with catalytically activated hydrogen to the bis(hydroxyethylsulfonylmethyl)aniline of the general formula (I), in which R and X denote hydrogen atoms and n denotes the number 2.

As for the procedure of the individual steps of the process according to the invention, details are given below:

1,2-, 1,3- or 1,4-bis(chloromethyl)benzene (A) is reacted in an aqueous medium without using organic solvents with mercaptoethanol in the presence of an acid-binding agent to give the corresponding bis(hydroxyethylmercaptomethyl)benzene (B):

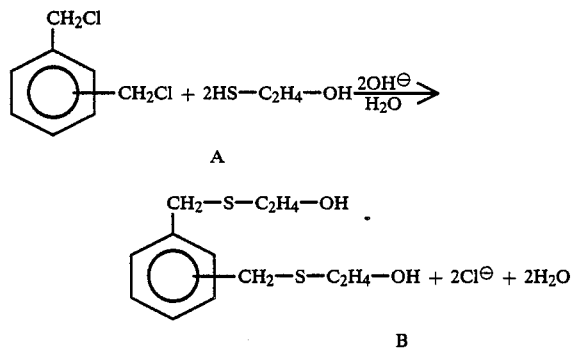

At least 2 mol of mercaptoethanol are required for the quantitative reaction of one mol of bis(chloromethyl)benzene. To obtain high yields in an industrially justifiable time, a molar excess of 10 to 100%, preferably 20 to 50%, of mercaptoethanol has proven advantageous.

Suitable acid-binding agents are the oxides, hydroxides and carbonates of the alkali metals and alkaline earth metals, preferably the hydroxides and carbonates of the alkali metals and also the oxides of the alkaline earth metals, potassium hydroxide or potassium carbonate and magnesium oxide being very particularly, suitable. As a rule, they are used in the equivalent ratio of 1:1 with respect to mercaptoethanol. A slight excess (up to about 30%) of acid-binding agent does not adversely effect the reaction and is therefore allowed.

The condensation is carried out at temperatures from about 40° to about 150° C., preferably about 70° to about 120° C., very particularly preferably at about 90° to 100° C., and is completed in a few hours. At temperatures above 100° C., the condensation must be carried out in the closed system under pressure.

The bis(hydroxyethylmercaptomethyl)benzenes (B) which are precipitated after the reaction as a solid or oil are isolated by filtration or phase separation, if necessary, although it is particularly advantageous to react them further in the form of the condensation mixture.

The oxidation of compounds (B) to the bis(hydroxyethylsulfonylmethyl)benzenes (C) is carried out using hydrogen peroxide in the presence of tungsten (VI) catalysts (sodium tungstate, tungsten trioxide):

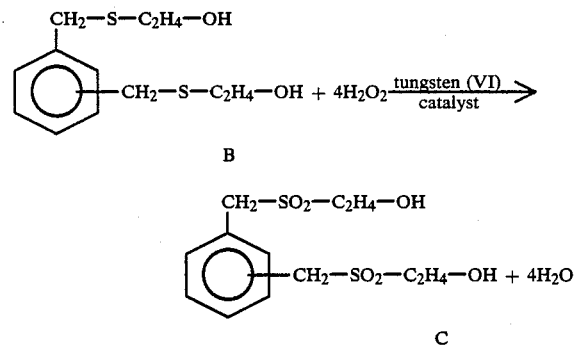

To this end, a solution of the isolated compound (B) in water or, particularly advantageously, directly the abovementioned aqueous condensation mixture formed is reacted at a pH of <7, preferably <4, after the addition of the catalyst (0.1 to 10 parts per mole of compound (B), preferably 1 to 3 parts) with at least the 4-fold molar amount of hydrogen peroxide, preferably the 4.4- to 5.6-fold molar amount, at temperatures from about 50° to about 120° C., preferably about 80° to about 100° C., and the mixture is stirred for another 2 to 20 hours, preferably 4 to 10 hours. The bis(hydroxyethylsulfonylmethyl)benzenes (C), which precipitate after cooling of the mixture to room temperature, are filtered off with suction, washed and dried.

Before nitrating the compounds (C), the hydroxyl groups of the substituents must be protected. This is done by esterification with sulphuric acid to give the half esters of the general formula (D):

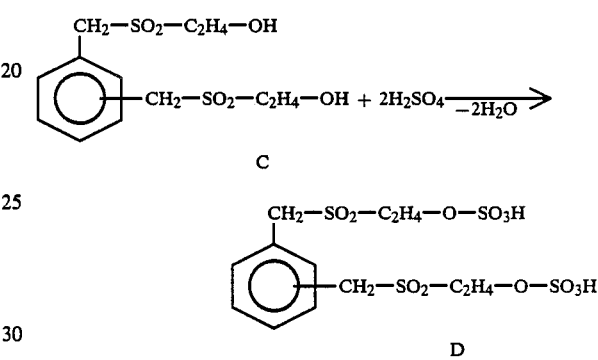

To complete the esterification, it is necessary to remove the reaction water, which is achieved according to the invention by using anhydrous sulfuric acid in at least a 4-fold, advantageously 5- to 7-fold, molar excess. Under these conditions, a quantitative reaction at a moderate temperature (about 30° to about 45° C.) is possible in a few hours.

The resulting sulfuric acid solution of the compounds of the formula (D) serves directly as the nitrating medium according to the invention. Isolation of the bis(sulfatoethylsulfonylmethyl)benzenes (D) brings no advantages. The nitration is carried out by the addition of at least the stoichiometric amount of high-percentage nitric acid, if necessary, as a mixture with anhydrous sulfuric acid (generally known as "mixed or nitrating acids") over a period of 2 to 10, preferably 3 to 6, hours at temperatures from about 0° to 60° C., preferably at about 45° C. To complete the nitration, it can be advantageous to use the nitric or nitrating acid in a small excess (5 to 20 mol percent):

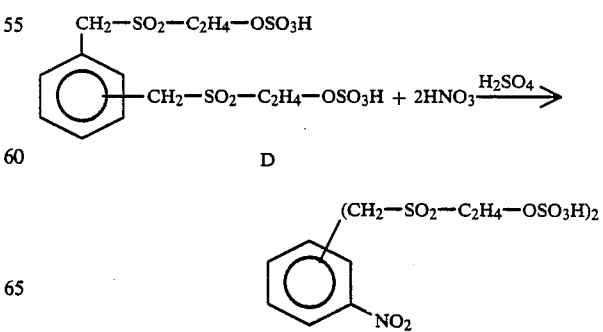

The bis(β-sulfatoethylsulfonylmethyl)nitrobenzene of the general formula E or I (R is 0, X is —SO₃H) present after the completed nitration in sulfuric acid solution is usually not isolated either according to the invention (if desired, it can be precipitated by salting out with, for example, sodium sulfate and separated off from the major amount of sulfuric acid by filtration), but is hydrolyzed after the addition of water (one- to six-fold amount by weight, preferably three- to four-fold amount by weight, relative to the total amount of sulfuric acid used), by refluxing the several hours (3 to 10 hours, preferably 4 to 6 hours at about 100° to about 120° C.) to give the free hydroxyethylsulfonylmethyl compound of the general formula (F):

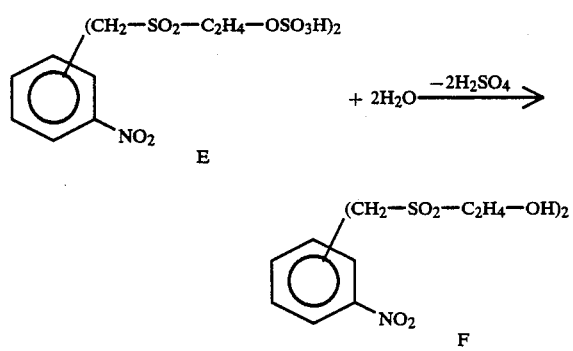

Upon cooling to temperatures from −5° C. to +10° C., the bis(hydroxyethylsulfonylmethyl)nitrobenzene (F) is precipitated. It is filtered off with suction, washed and, if necessary, dried.

For the final reduction of the nitro group, either an aqueous reduction with iron (Béchamp reduction) or, particularly advantageously, an aqueous hydrogenation with catalytically activated hydrogen can be used. Not only customary nickel catalysts but also commercially available noble metal catalysts, for example platinum or palladium on inert supports, preferably on activated carbon having a high specific surface area, are suitable catalysts.

The reduction proceeds at elevated temperatures (about 70° to about 120° C., preferably about 80° to 100° C.) in an aqueous solution or suspension in a few hours (in 1 to 5 hours, preferably in 1.5 to 3 hours in the elevated temperature range) quantitatively and provides, at the reduction temperature, aqueous solutions of the desired bis(hydroxyethylsulfonylmethyl)aniline compounds of the general formula G or I (where R and X are hydrogen), from which the suspended iron oxide hydrates (in the case of Béchamp reduction) or the hydrogenating catalyst can be advantageously separated off by clarifying filtration:

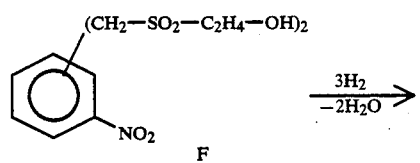

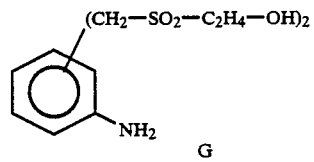

From the clarified filtrate, the bis(hydroxyethylsulfonylmethyl)aniline compounds, possibly after concentration by distilling off water in vacuo, can be precipitated by cooling to temperatures of −5° to +20° C. and/or salting out with, for example, sodium chloride or sodium sulfate and be isolated by filtration or centrifuging.

The yields and selectivities are in all steps surprisingly high and, in most cases, almost reach the values expected by theory.

The novel bis(hydroxyethylsulfonylmethyl)anilines of the general formula I (where R and X are H) are highly suitable for use as diazo components for fiber-reactive azo dyes having a particularly high degree of fixation and thus make a significant technical advance in this important class of dyes possible.

The examples which follow are intended to illustrate the invention in more detail without limiting it thereto. Parts are by weight, unless noted otherwise.

EXAMPLE 1

A stirred mixture of 1,000 parts of water, 350 parts of 1,4-bis(chloromethyl)benzene (p-xylylene dichloride), 437 parts of mercaptoethanol and 392 parts of potassium carbonate is heated at 90° to 95° C. for 3 hours. After that time, a uniform HPLC chromatogram is obtained and the starting material can no longer be detected. The mixture is cooled to 10° C., the precipitate is filtered off with suction, washed with ice water until the filtrate is neutral and dried in vacuo at 60° C.

This gives 512 parts of 1,4-bis(hydroxyethylmercaptomethyl)benzene of the formula

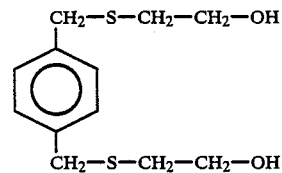

of melting point 90° to 92° C.

Analysis: S: 24.9/24.8% (calculated 24.8%); Cl: <0.03% (calculated 0.0%).

EXAMPLE 2

200 parts of magnesium oxide are added to a mixture of 700 parts of 1,2-bis(chloromethyl)benzene (o-xylylene dichloride), 2,000 parts of water and 756 parts of mercaptoethanol at 60° C. over a period of 15 minutes with stirring, slight cooling being necessary for maintaining the temperature. The mixture is subsequently heated at 95° to 100° C. for 3 hours, after which an HPLC chromatogram indicates complete conversion. The mixture is cooled to 15° C., the oil which separates out is separated off, washed by stirring it in deionized water and another phase separation, and the organic phase is dried by distillation in a vacuum of 20 torr until no more distillate comes over.

This gives 1,030 parts of 1,2-bis(hydroxyethylmercaptomethyl)benzene of the formula

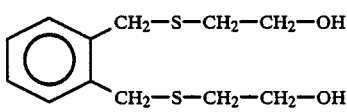

as a colorless liquid which cannot be distilled without decomposition.

Analysis: S: 24.95/24.85% (calculated 24.8%); Cl: <0.03% (calculated to 0.0%).

EXAMPLE 3

The procedure of the previous Example 2 is repeated, except that 1,2-bis(chloromethyl)benzene is replaced by 1,3-bis(chloromethyl)benzene (m-xylylene dichloride) to give, in a comparable yield, 1,3-bis(hydroxyethylmercaptomethyl)benzene of the formula

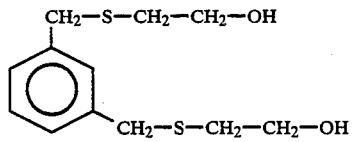

as a colorless, undistillable oil.

EXAMPLE 4

To a stirred initial mixture of 103.2 parts of 1,4-bis(hydroxyethylmercaptomethyl)benzene (prepared according to Example 1), 20 parts of glacial acetic acid and 1.6 parts of sodium tungstate are added dropwise at 90° C. over a period of 1 hour 168 parts of 35% strength aqueous hydrogen peroxide, stirring is continued for 3 hours at 90° to 95° C. (an HPLC chromatogram indicates complete oxidation), the mixture is cooled to 20° C., the precipitate is isolated by filtration with suction, washed with ice water until the filtrate is neutral and dried in vacuo at 80° C.

This gives 125.0 parts of 1,4-bis(hydroxyethylsulfonylmethyl)benzene of the formula

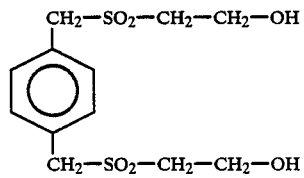

in the form of colorless crystals of melting point 213° to 215° C. Its purity (HPLC) is 98.7 %.

EXAMPLE 5

The procedure of the previous example 4 is repeated, except that 1,4-bis(hydroxyethylmercaptomethyl)benzene is replaced by the same amount of the 1,3 isomer to give 105.1 parts of 1,3-bis(hydroxyethylsulfonylmethyl)benzene of the formula

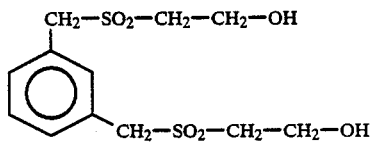

as colorless crystals melting at 111° to 112° C. and having a purity (HPLC) of 99.1%.

EXAMPLE 6

420 parts of 35% strength aqueous hydrogen peroxide are added to a mixture of 258 parts of 1,2-bis(hydroxyethylmercaptomethyl)benzene, 250 parts of 10% strength sulfuric acid and 4 parts of sodium tungstate, starting at 60° C., at such a rate that the internal temperature does not exceed 95° C. (about 70 minutes). Stirring is then continued for 5 hours at 95° C. (checked by HPLC for complete conversion), the mixture is cooled to 10° C., and the precipitate is isolated by filtration. Washing with ice water followed by drying in vacuo at 80° C. gives 304 parts of 1,2-bis(hydroxyethylsulfonylmethyl)benzene.of the formula

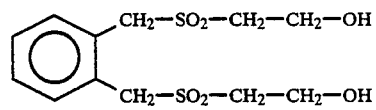

in the form of colorless crystals melting at 116° to 118° C. The purity (HPLC) is 98.4%.

EXAMPLE 7 (ONE-POT PROCESS)

700 parts of 1,4-bis(chloromethyl)benzene (p-xylylene dichloride), 750 parts of mercaptoethanol and 1,500 parts of water are mixed with stirring and heated to 50° to 55° C. 200 parts of magnesium oxide are then stirred in over a period of 30 minutes in such a manner that the internal temperature does not exceed 60° C., the mixture is subsequently heated at 90° to 95° C. for 3 hours (according to the HPLC chromatogram the starting compound is completely converted), brought to a pH of 7.0 with 2n sulfuric acid and cooled to 60° C. 150 parts of glacial acetic acid and 8 parts of tungsten trioxide are then added in succession and 1,250 parts of hydrogen peroxide, 35% strength, are then added dropwise over a period of 60 minutes at a constant rate. During this addition, the internal temperature must not reach 90° C. Stirring is continued for about 5 hours at 90° to 95° C., until a sample shows a uniform final product in the HPLC chromatogram, the mixture is cooled to 20° C., and the precipitate is isolated by filtration. Washing with ice water followed by drying in vacuo at 100° C. gives 842 parts of 1,4-bis(hydroxyethylsulfonylmethyl)benzene of the formula

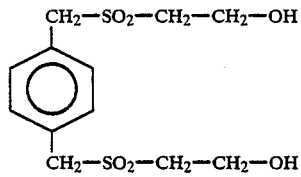

in the form of slightly yellowish crystals of melting point 210° to 212° C. and a purity (HPLC) of 96.9%.

The procedure is repeated, except that 1,4-bis(chloromethyl)benzene is replaced by 1,2- or 1,3-bis(chloromethyl)benzene to give the 1,2- or 1,3-bis(hydroxyethylsulfonylmethyl)benzene in comparable yield and quality.

EXAMPLE 8

80.5 parts of 1,4-bis(hydroxyethylsulfonylmethyl)benzene are stirred into 612.5 parts of 100% strength sulfuric acid, and the mixture is heated at 35° to 40° C. until a sample shows quantitative esterification in the HPLC chromatogram (about 4 to 5 hours). 57 parts of a mixture of 30 parts by weight of 100% strength nitric acid and 70 parts by weight of 100% strength sulfuric acid (so-called "M3 acid") are then added dropwise over a period of 4 hours at 30° to 40° C., stirring is continued for 2 hours at 45° C. until the nitration is completed (checked by HPLC chromatogram), and the reaction mixture is then decomposed by pouring it into 2,500 parts of cold water. The resulting aqueous acidic solution is then refluxed (about 110° C.) for 5 hours to hydrolyze the sulfuric ester groups, 5 parts of activated carbon are then added, the mixture is clarified and the clarified filtrate is cooled to 0° to 5° C. with stirring. The resulting precipitate is filtered off with suction, washed neutral and dried in vacuo at 80° C. This gives 89.0 parts of 2,5-bis(hydroxyethylsulfonylmethyl)nitrobenzene of the formula

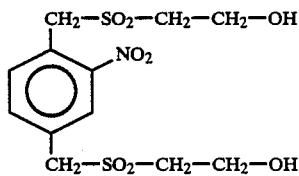

in the form of colorless crystals of melting point 125° to 126.5° C., the purity of which (HPLC) is 98.8%.

The procedure is repeated, except that the "M3 acid" is replaced by 17.5 parts of 98% strength nitric acid to give a comparable result.

EXAMPLE 9

Example 8 is repeated, except that 1,4-bis(hydroxyethylsulfonylmethyl)benzene is replaced by the 1,3 isomer to give 82.4 parts of 2,4-bis(hydroxyethylsulfonylmethyl)nitrobenzene of the formula

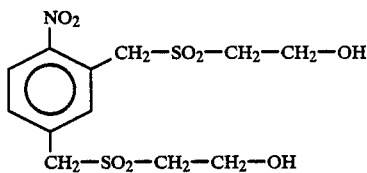

as slightly yellow crystals of melting point 211° to 212° C. having a purity (HPLC) of 97.9%.

EXAMPLE 10

Example 8 is repeated, except that 1,4-bis(hydroxyethylsulfonylmethyl)benzene is replaced by the 1,2 isomer to give 85.4 parts of 3,4-bis(hydroxyethylsulfonylmethyl)nitrobenzene of the formula

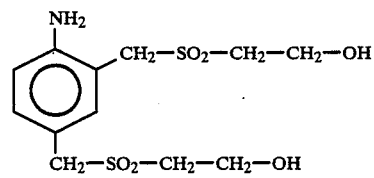

as colorless crystals of melting point 126° to 128° C. having a purity (HPLC) of 98.2%.

EXAMPLE 11

100 parts of 2,4-bis(hydroxyethylsulfonylmethyl)nitrobenzene are added at a constant rate over a period of 30 minutes with stirring to a mixture heated to 80° to 85° C. and consisting of 40 parts of iron powder and 200 parts of water, the reaction temperature being maintained at 80° to 85° C. during the addition. After the addition is completed, stirring is continued for 30 minutes, the pH is adjusted to 8.5 with aqueous sodium carbonate solution, and the mixture is clarified while hot by removing the precipitated iron hydroxide. The filter residue is washed twice with a small amount of hot water. The combined filtrates are subsequently concentrated in vacuo to 150 parts by volume and subsequently cooled to 0° to 5° C. with stirring. The slightly brownish precipitate is isolated on a nutsche filter, covered with a small amount of ice water and dried in vacuo at 60° C. This gives 84.7 parts of 2,4-bis(hydroxyethylsulfonylmethyl)aniline of the formula $$\text{structure with } NH_2, CH_2-SO_2-CH_2-CH_2-OH \text{ groups}$$

of melting point 183° to 185° C. and a purity (by diazotization) of 99.5%.

Analysis: C: 42.6% (calculated 42.72%), H: 5.85% (calculated 5.68%), N: 4.05% (calculated 4.15%), S: 18.95% (calculated 19.00%).

EXAMPLE 12

Example 11 is repeated, except that 2,4-bis(hydroxyethylsulfonylmethyl)nitrobenzene is replaced by the 2,5 isomer to give 2,5-bis(hydroxyethylsulfonylmethyl)aniline of the formula $$\text{structure with } NH_2, CH_2-SO_2-CH_2-CH_2-OH \text{ groups}$$

as beige-colored crystals of melting point 196° to 198° C. in comparable yield and quality. The formula given above is confirmed by elemental analysis.

EXAMPLE 13

A hydrogenation autoclave is charged with 3,000 parts of water and 150 parts of 2,5-bis(hydroxyethylsulfonylmethyl)nitrobenzene, and 10 parts of noble metal catalyst (5% palladium on carbon) are added. The autoclave is sealed, and the gas space is freed from oxygen and nitrogen by purging three times first with nitrogen and then with hydrogen.

Subsequently, 40 bar of hydrogen are injected, and the mixture is heated to 90° C. The hydrogen pressure is maintained at 40 to 45 bar by constant additional injection of hydrogen. After 2 hours at 90° C., the absorption of hydrogen ceases. The autoclave contents are cleared from the catalyst while hot through a pressure filter, and the filtrate is cooled to 0° to 5° C. with stirring. The precipitated colorless crystals are filtered off with suction, washed with a small amount of ice water and dried in vacuo at 60° C. This gives 110 parts of 2,5-bis-(hydroxyethylsulfonylmethyl)aniline of the formula

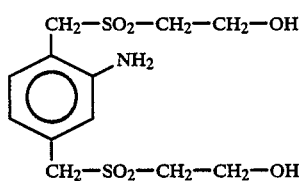

of melting point 198° to 199° C. having a purity of 99.9% (determined by diazotization).

EXAMPLE 14

Example 13 is exactly repeated, except that instead of 3,000 parts of water the aqueous mother liquor (about 3,050 parts) formed according to Example 13 and instead of fresh catalyst the palladium catalyst separated off from the hydrogenation mixture by clarifying filtration are used.

This gives 122 parts of 2,5-bis(hydroxyethylsulfonylmethyl)aniline of melting point 198° to 199° C. and a purity (diazotization) of 99.8%.

EXAMPLES 15 TO 23

The procedure as described in Examples 13 and 14 is repeated, using each time 150 parts of 2,5-bis(hydroxyethylsulfonylmethyl)nitrobenzene as well as each time the aqueous mother liquor and the palladium catalyst of the previous batch to give each time about 128 parts of 2,5-bis(hydroxyethylsulfonylmethyl)aniline of melting point 197° to 199° C. and a purity (diazotization) of >99%, i.e., mother liquor and catalyst can each be recycled at least 10 times without deterioration of the product or reduction of the yield.

EXAMPLE 24

The procedure of Example 13 is repeated, except that the palladium catalyst is replaced by a customary platinum or nickel supported catalyst to give 2,5-bis(hydroxyethylsulfonylmethyl)aniline in comparable yield and quality.

EXAMPLE 25

The procedure of Example 13 is repeated, except that 2,5-bis(hydroxyethylsulfonylmethyl)nitrobenzene is replaced by the 3,4 isomer (cf. Example 10) to give 3,4-bis(hydroxyethylsulfonylmethyl)aniline of the formula

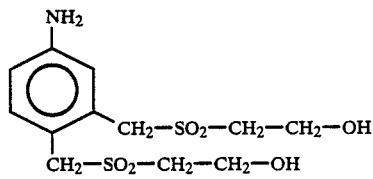

in the form of colorless crystals of melting point 168° to 171° C. having a purity (diazotization) of 99.2%.

We claim:

1. A bis(hydroxyethylsulfonylmethyl)aniline of the formula

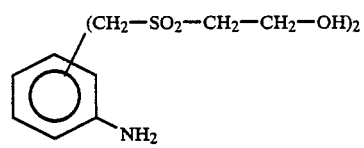

in which the two side chains —CH$_2$—SO$_2$—CH$_2$—CH$_2$—OH are in the ortho-, meta- or para-position relative to one another and the amino group is in the 4-position in the case where the two side chains mentioned are in the 1,2-or 1,3-position.

2. A bis(hydroxyethylsulfonylmethyl)nitrobenzene of the formula

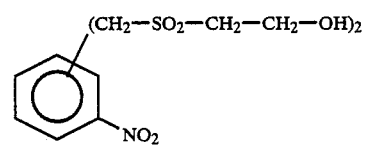

in which the two side chains —CH$_2$—SO$_2$—CH$_2$—CH$_2$—OH are in the ortho-, meta- or para-position relative to one another and the nitro group is in the 4-position in the case where the two side chains mentioned are in the 1,2-or 1,3-position.

3. A process for the preparation of bis(hydroxyethylsulfonylmethyl)anilines of the formula

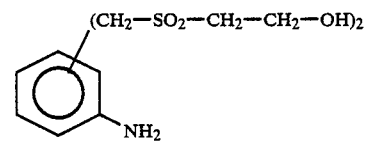

in which the two side chains —CH$_2$—SO$_2$—CH$_2$—CH$_2$—OH are in the ortho-, meta- or para-position relative to one another and the amino group is in the 4-position in the case where the two side chains mentioned are in the 1,2-or 1,3-position, which comprises reacting 1 mol of xylylenedichloride (1,2-, 1,3- or 1,4-bis(chloromethyl)benzene) with at least 2 mol of mercaptoethanol at temperatures from about 40° to about 150° in an aqueous medium in the presence of an acid-binding agent to give the corresponding bis(hydroxyethylmercaptomethyl)benzene of the formula

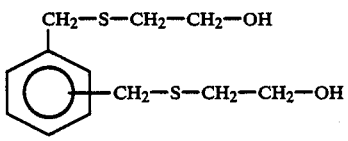

in which the two side chains are in the ortho-, meta- or para-position relative to one another, oxidizing this product with at least 4 mol of hydrogen peroxide at temperatures from about 50° to about 120° C. at a pH <7 in the presence of tungsten(VI) compounds as a catalyst to give the corresponding bis(hydroxyethylsulfonylmethyl)benzene of the formula

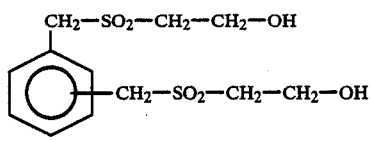

in which the two side chains are in the ortho-, meta- or para-position relative to one another, converting this product with at least 4 mol of anhydrous sulfuric acid at temperatures of about 30° to about 45° C. to the corresponding bis(sulfuric ester), nitrating the latter with at least the stoichiometric amount of high-percentage nitric acid at temperatures from about 0° to about 60° C. to give the bis(sulfatoethylsulfonylmethyl)nitrobenzene of the formula

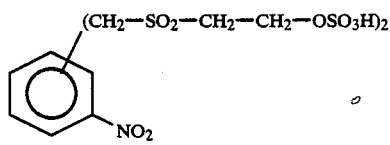

in which the two side chains —$CH_2$—$SO_2$—$CH_2$—$CH_2$—$OSO_3H$ are in the ortho-, meta- or para-position relative to one another and the nitro group is in the 4-position in the case where the two side chains mentioned are in the 1,2-or 1,3-position, hydrolyzing this product after the addition of water by heating to give the corresponding bis-(hydroxyethylsulfonylmethyl)nitrobenzene and reducing the latter, after isolation of the intermediate, to the corresponding bis(hydroxyethylsulfonylmethyl)aniline.

4. The process as claimed in claim 3, wherein the acid-binding agents used are the oxides, hydroxides or carbonates of the alkali metals or alkaline earth metals.

5. The process as claimed in claim 3, wherein the oxidation is carried out in the presence of sodium tungstate or tungsten trioxide.

6. The process as claimed in claim 3, wherein the reduction with iron is carried out in an aqueous medium.

7. The process as claimed in claim 3, wherein the reduction is carried out in an aqueous medium with catalytically activated hydrogen.

8. The process as claimed in claim 3, wherein the hydrolysis is carried out by refluxing to temperatures from about 100° to about 120° C.

9. A compound of the formula

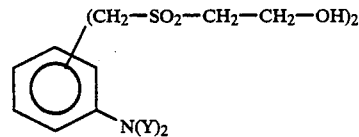

in which Y denotes a hydrogen or oxygen atom, the two side chains —$CH_2$—$SO_2$—$CH_2$—$CH_2$—$OH$ are in the ortho-, meta- or para-position relative to one another, and the $N(Y)_2$ group is in the 4-position in the case where the two side chains mentioned are in the 1,2- or 1,3-position.

* * * * *